United States Patent [19]

Martin et al.

[11] Patent Number: 4,675,105
[45] Date of Patent: Jun. 23, 1987

[54] SYSTEM FOR OBTAINING A HOMOGENEOUS ABSORBENT BED IN A CHROMATOGRAPHIC COLUMN

[75] Inventors: Charles W. Martin, Monroe County, Ill.; Yehuda Shalon, St. Louis County, Mo.

[73] Assignee: HT Chemicals, Inc., St. Louis, Mo.

[21] Appl. No.: 872,632

[22] Filed: Jun. 10, 1986

Related U.S. Application Data

[63] Continuation of Ser. No. 714,974, Mar. 22, 1985, abandoned.

[51] Int. Cl.$^4$ ............................................. B01D 15/08
[52] U.S. Cl. .................................. 210/198.2; 210/656
[58] Field of Search ..................... 100/295; 141/73, 80; 215/231, 363, 355; 210/198.2, 656

[56] References Cited

U.S. PATENT DOCUMENTS

| | | | |
|---|---|---|---|
| 2,178,686 | 11/1939 | Georgier et al. | 215/363 X |
| 4,033,380 | 7/1977 | Weber | 138/96 T |
| 4,309,286 | 1/1982 | Lenihan, Jr. et al. | 210/198.2 |
| 4,350,595 | 9/1982 | Gunkel | 210/198.2 X |
| 4,390,043 | 6/1983 | Ward | 138/89 |
| 4,470,910 | 9/1984 | Quemerais et al. | 210/198.2 X |
| 4,549,584 | 10/1985 | Morin et al. | 210/198.2 X |
| 4,578,193 | 3/1986 | Shepherd | 210/198.2 X |
| 4,587,014 | 5/1986 | America | 210/198.2 |

Primary Examiner—Stephen Marcus
Assistant Examiner—Mark Thronson
Attorney, Agent, or Firm—Paul M. Denk

[57] ABSTRACT

A slurry compressor for obtaining a homogeneous absorbent bed in a chromatographic column wherein said compressor includes a shaped member having external dimensions slightly less than the internal dimensions of the column in which the bed of particles is being compressed. The compressor having an innermost portion and an outermost portion, integrally connected, the innermost portion being a solid segment incorporating a lower surface, while the outermost portion includes a hollowed interior forming a walled structure extending integrally from the solid segment, with the walled structure flaring slightly outwardly to assure a reasonably snug contact with the inner surface and interior wall of the associated column.

4 Claims, 4 Drawing Figures

SYSTEM FOR OBTAINING A HOMOGENEOUS ABSORBENT BED IN A CHROMATOGRAPHIC COLUMN

This is a continuation application of the application having Ser. No. 714,974, filed on Mar. 22, 1985, and now abandoned.

BACKGROUND OF THE INVENTION

This invention relates generally to a particularly styled compressor for application in the initial compacting of the slurry of the absorbent bed of particles used within chromatographic columns as employed in chromatography. The type of chromatography of concern relates to high pressure liquid chromatography (HPLC), where the columns to be packed can be employed in analytical, semipreparative, preparative, or a process column for use in chromatography. As is well known in the art, chromatographic columns are generally fabricated of some metal, such as stainless, in the tubular form, and contain a slurried bed of particles that function to separate various chemicals that are passed through it, at pressures that may range anywhere from just higher than atmospheric and up to the extremely high pressures in the range of 2000 to 4000 psi. Through this function the chemical or chemicals passing through the absorbent bed are generally separated into their desired elements, or constituents, so that the various elements desired can be obtained, or analysis of the chemical passing through the columns can be made. As one can readily understand, the degree of compactness of the slurry of the absorbent bed contained within the chromatographic column or columns must be maintained at a very high and required density, in order to achieve the most efficient and effective results from the chromatography procedure.

The art of chromatography has long been available to the field of chemistry. Generally, the packing of the slurry bed within the preparative columns was usually performed by the suspension of the bed particles in a liquid of low viscosity and density and which was forced into the columns at a constant flow-rate, usually in an upward vertical direction. Thus, while this generalized statement of the prior art indicates that the slurry bed, in the past, was packed under pressure within the chromatographic columns, that method of packing normally could not attain the fine degree of compactness for the bed within the column, and within that range of density as not only as desired, but required, in order to attain the most effective usage of the columns during the performance of a chromatographic process. And, where dry packing of the columns is required, as has also been done in the prior art, normally the absorbent bed of particles was simply delivered into the column, and packed in this manner. But, as can be readily understood, technical difficulties would usually arise with such packed columns, said during their usage, normally exhibited in the formation of bubbles or air pockets, be they ever so small, yet captured within the packed bed.

In view of the foregoing, it is the principal object of this invention to provide a compressor, preferably one fabricated of a polymer, or other material, or perhaps even of a metal such as stainless, and which is constructed to particular dimensions to provide for its very contiguous arrangement within the interior of the column after an ample supply of the absorbent material has been deposited therein, and which compressor is then subjected to hydraulic or otherwise pressure to provide for a full compacting of the bed into its more effective and efficient usable state.

Another object of this invention is to provide a compressor that is particularly useful when applied in conjunction with a liquified slurry of an absorbent bed of particles as delivered into chromatographic column(s) during their initial or prepacking.

A further object of this invention is to provide a particularly effective compressor for use in conjunction with a pair or more of chromatographic columns that are coupled together, filled with that quantity of a slurry of the absorbent bed of material to an amount that is designed for providing for at least the fully compaction of a bed within at least the bottom column, to provide for a prepacked preparative column that will be ready for providing very precise functioning for chemical separation, absorption, or analysis, during its use in the performance of chromatography.

These and other objects will become more apparent to those skilled in the art upon reviewing the summary of this invention, and upon undertaking a study of the description of the preferred embodiment, in view of the drawing.

SUMMARY OF THE INVENTION

This particular invention contemplates the fabrication of a compressor, for use, as previously explained, for providing prepacked chromatographic columns for application for chemical analysis. The compressor is fabricated, preferably, of a polymeric material, such as Teflon, and which is shaped of two integral components, namely an innermost portion that is comprised of a solid segment, and having an outermost portion which incorporates a cavity within its interior, and thereby forming a form of walled structure that extends integrally from the said innermost solid segment portion. The walled structure may flare slightly, outwardly, to assure a reasonable snugness and contiguity with the interior surface of the column in which the compressor locates, after an ample quantity of the slurry or dry bed of absorbent material will have just previously been inserted therein. Thus, when the column is then closed, as through capping, and a hydraulic or other form of pressure is applied therein, above the location of the compressor, the compressor will be pressed substantially against the bed of material, and compact it into a degree of compaction predetermined by the amount of pressure that is applied upon the combined bed and said compressor. In addition, where the slurry bed of material incorporates a solvent, to form that slurry bed to facilitate its packing, the flared walled structure of the compressor will prevent the bypassing of any of the particles of the absorbent bed thereby, as the compressor presses upon the forming bed, while the solvent forming the slurry will seep out of the other end of the column in order to provide for a more fully compacted state for the particles that are intended to form the absorbent bed. And, in order to achieve a fuller compacted state for an absorbent bed within a preparative column, a pair or more of the columns may be joined together, with the bottom and next adjacent column being filled with that quantity of the slurry predetermined to provide for a fully compacted bed of particles within the bottom column being prepared. Under this condition, when the compressor is located into position, and subjected to exceedingly high hydraulic or otherwise fluid pressure, either of liquid or air, it has the tendency of fully compacting the bed of particles within that bottom column, allowing the excess solvent to seep out of the column end through its arranged frit, while packing the particles thereabove during this prepacking operation. Under this procedure, the bottom column will then be fully compacted with a bed of absorbent particles to that density determined necessary to provide a chromatographic column required for analysis of particular chemicals, or absorbent of select of their ingredients, in order to afford highly efficient and effective chromatographic analysis of the chemical or chemicals under study. Then, by simply removing the second and other columns, from the bottom column, a frit and its O-rings, in addition to the column end, may be applied, thereby providing a preparative column that is readied for precise application for analysis or separation of fractions or purification of chemicals of the particular chemical(s) under study.

DESCRIPTION OF THE PREFERRED EMBODIMENT

Figure 1:
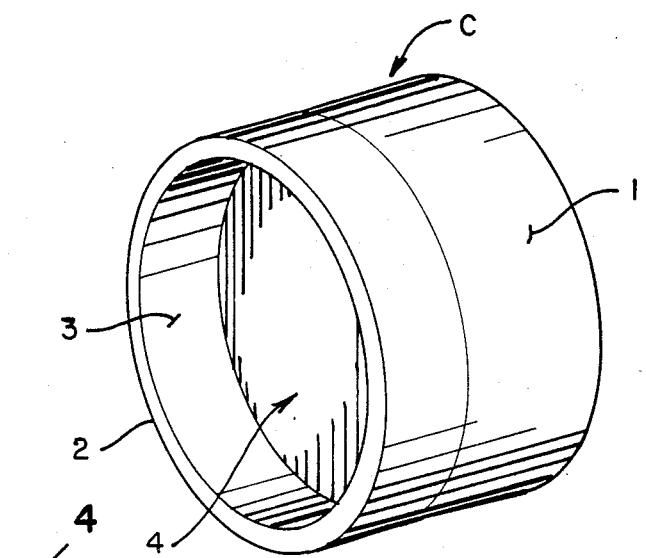
FIG. 1 provides a perspective view of the compressor of this invention.
Figure 2:
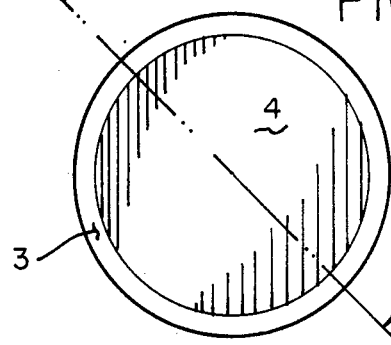
FIG. 2 is a top or left end view thereof.
Figure 3:
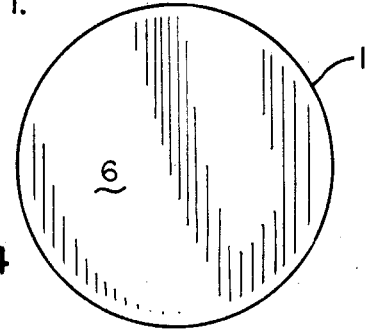
FIG. 3 is a bottom, or right end view thereof.
Figure 4:
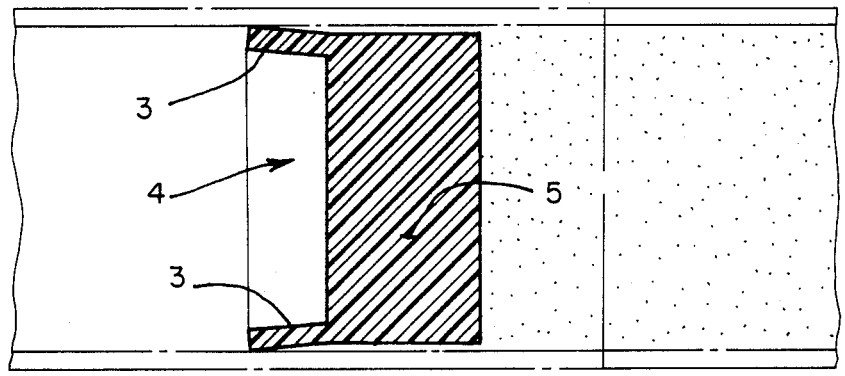
FIG. 4 is a sectional view of the compressor taken long the line 4—4 of FIG. 2, and showing in phantom line schematically a part of the chromatographic and reservoir columns forming the hydraulic-like cylinder for this system.

In referring to the drawings, and in particular FIG. 1, there is disclosed the slurry compressor C of this invention and which shows a cylindrically designed element, having what is identified as the innermost portion 1 that fits initially within the column in which the bedded material is to be compacted. The innermost portion 1 is integrally connected with the outermost portion 2 which in this particular instance, is shown as a cylindrical like member having a walled structure, as at 3, and arranging an internal cavity, as at 4, therein. The innermost portion 1 is formed as a solid segment 5, which is more aptly depicted in FIG. 4. These innermost and outermost portions are integrally formed as a single unit, as can be seen in said latter figure. The innermost portion 1 has a flattened lower surface 6 which is designed to be arranged snugly within the column in which the slurry is being prepared, and to fully compact against the forming bed during the application of hydraulic or other pressure, even at rather excessive pressures, such as previously defined, there against during the bed preparation stage. As can also be seen, as in FIG. 4, the walled structure 3 flares slightly outwardly, and thereby biases rather tightly against the interior surface of the column in which the bed is being prepared. Thus, when excessive pressures are exerted upon the forming bed, the particles of the bed will be tightly compressed by means of biasing against the bottom surface 6 of the compressor, with some or all of the solvent forming the slurry for the bed exiting out of the other end of the column, to assure that a proper density of particles will be compacted together in the formation of the bed for the preparative or other identified column. While the flared walled structure 3 for the compressor, as previously explained, will tightly press against the walls of the column, during bed preparation, the tightness will not be so great that the compressor cannot be removed after the bed has been fully compacted to its desired density.

As can be seen in the drawings, and as previously explained herein, the compressor preferably will be formed of a polymer, or polymeric material, such as a Teflon, or in the alternative, it is likely that it may be made of other materials, as desired, provided that the application of the compressor will provide an effective means of compaction of the bed during its formation. Forming the compressor of Teflon facilitates removal after application.

In slurry packing, or the wet packing method of columns, the procedure generally is defined as a filling of a chromatographic column by use of a suspension of particles such as a normal phase, or plain silica gel, or a reverse phase, or coated silica gel, as absorbents, in a solvent or a mixture of solvents with a defined viscosity and density. The particles are forced into the column either at a predetermined linear velocity, as previously explained as the flow rate, or by a mechanical method of compression, such as through the use of the slurry compressor of this invention. The main object of the slurry packing is to achieve a homogeneous absorbent bed for the chromatographic separation. The slurry packing is essential for packing of the particles of less than 20–30 microns. This is achieved in order to avoid particle size segmentation and agglomeration. When such deleterious effects are obtained in the bed, during its formation, it often results in a heterogenous packing bed which greatly impairs and reduces the efficiency of the chromatographic separations performed through usage of the preparative column.

Generally, analytical high pressure liquid chromatography (HPLC) columns, and semi-preparative columns of internal diameters of less than one inch are best prepared by using the high flow-linear velocity method of slurry packing. Preparative columns, having internal diameters greater than one inch, cannot be effectively packed by the above method due to the physical limitations of the high pressure solvent delivery systems, such as the pumps, required to achieve the minimum linear velocity for maximum packing efficiency. Hence, columns of interior diameters greater than one inch are best and most effectively packed by an axial compression method.

The packing of modular HPLC preparative columns is achieved by joining together that column to be packed with another modular column which will serve as a reservoir column with about 4 to 5 times the greater volume than the column being packed. The combined columns together form a hydraulic like cylinder. The actual column packing is achieved by the axial compression and it is accomplished by utilizing a suitable movable hydraulic piston driven by a high pressure amplification, such as a fluid driven pump as of the type produced by Haskal Company, under Model DSTV No. 122. The amount of solvent needed for slurry packing is usually 4 to 5 times the weight of the silica gel to be packed. Therefore, the combined columns, as previously explained, must contain enough volume to accommodate the total slurry to be used in the packing system, or in the hydraulic cylinder arrangement. As the fluid pressure is applied to the cylinder, movement of the packing piston, such as the slurry compressor of this invention, compresses the slurry into a homogeneous and uniform bed of particles. The density of the packed bed will be determined by the length of the bed formed, as well as by the applied pressure against the piston or compressor during the application of its force upon the slurry during the packing process. Upon completion of the packing process, the packed column is then carefully taken from the combined hydraulic cylinder and is separated from the reservoir or adjoining column portion. The packed column, as previously explained, is then furnished with a frit, the necessary O-rings, and a lid or column end, and is then ready for usage. Once the packed column is reassembled with the proper frits, rings, and end plates, the packed column is reequilibrated under conditions of high pressure and a flow of solvent, usually with a washing solvent, to remove the remains of any slurry packing solvent or solvents contained within the bed, before any testing or evaluation is performed on the packed column, or before it becomes finally certified for usage.

Variations or modifications to the subject matter of this invention, namely, the compressor, or its method of usage, may occur to those skilled in the art upon reviewing the subject matter of this invention. Such variations or modifications, if within the spirit of this invention, are intended to be encompassed within the scope of any claims to patent protection issuing upon this invention. The description of the preferred embodiment set forth herein, in addition to the drawings, are provided for illustrative purposes only.

Having thus described the invention what is claimed and desired to be secured by Letters Patent is:

1. A system for obtaining a homogeneous absorbent bed of particles in a chromatographic column, said system comprising a chromatographic column in which the absorbent bed is to be packed, a reservoir column containing a quantity of the absorbent bed, said chromatographic and reservoir columns being internally in communication with each other, said chromatographic and reservoir columns together forming a hydraulic-like cylinder, a slurry compressor contained in said hydraulic-like cylinder and subjected to pressure therein to compact the absorbent bed within said chromatographic column, said compressor including a shaped member having external dimensions slightly less than the internal dimensions of the hydraulic-like cylinder, said compressor having an innermost portion and a outermost portion, said portions being integral, the innermost portion being a solid segment incorporating a lower surface disposed for compressing against the bed of particles, said outermost portion having a hollowed interior forming a walled structure extending from the solid segment forming the innermost portion, and said walled structure flaring slightly outwardly to assure a resonable snugness and contiguity of the compressor with the interior wall of the hydraulic-like cylinder to assure the forced compaction of the compressor against the bed, while substantially preventing fluid from bypassing the compressor during compaction.

2. The invention of claim 1 and wherein the interior of the column in which the compressor is applied being round, and the shape of the compressor is a corresponding circular.

3. The invention of claim 2 and wherein said compressor being formed of a polymer.

4. The invention of claim 1 and wherein the integral innermost and outermost portions forming the compressor having a length, with the innermost portion having a length greater than the length of the outermost portion of the formed compressor.

* * * * *